United States Patent
Kamiyama et al.

(10) Patent No.: US 8,339,593 B2
(45) Date of Patent: Dec. 25, 2012

(54) SYSTEM AND METHOD OF TWO-STEPPED LASER SCATTERING DEFECT INSPECTION

(75) Inventors: Eiji Kamiyama, Tokyo (JP); Takehiro Tsunemori, Tokyo (JP); Kazuhiro Yamamoto, Tokyo (JP); Kenji Aoki, Tokyo (JP)

(73) Assignee: Sumco Corporation, Tokyo (JP)

( * ) Notice: Subject to any disclaimer, the term of this patent is extended or adjusted under 35 U.S.C. 154(b) by 482 days.

(21) Appl. No.: 12/571,791

(22) Filed: Oct. 1, 2009

(65) Prior Publication Data
US 2010/0085561 A1    Apr. 8, 2010

(30) Foreign Application Priority Data
Oct. 6, 2008 (JP) .................. 2008-259804

(51) Int. Cl.
*G01N 21/00* (2006.01)
(52) U.S. Cl. .................. 356/237.2; 356/237.5
(58) Field of Classification Search ..... 356/237.2–237.6
See application file for complete search history.

(56) References Cited

U.S. PATENT DOCUMENTS
5,712,701 A    1/1998    Clementi et al.
6,118,525 A    9/2000    Fossey et al.
6,292,259 B1   9/2001    Fossey et al.
7,280,200 B2 * 10/2007   Plemmons et al. ........ 356/237.3

FOREIGN PATENT DOCUMENTS
WO    2006/066207    6/2006

* cited by examiner

*Primary Examiner* — Gregory J Toatley
*Assistant Examiner* — Rebecca C Bryant
(74) *Attorney, Agent, or Firm* — Greenblum & Bernstein, P.L.C.

(57) ABSTRACT

A laser scattering defect inspection system includes: a stage unit that rotates a workpiece W and transports the workpiece W in one direction; a laser light source that emits a laser beam LB toward the workpiece W mounted on the stage unit; an optical deflector that scans the laser beam LB emitted from the laser light source on the workpiece W; an optical detector that detects the laser beam LB scattered from the surface of the workpiece W; a storage unit that stores defect inspection conditions for each inspection step of a manufacturing process of the workpiece W, where the conditions include the rotation speed and the moving speed of the workpiece W by the stage unit, the scan width on the workpiece W and the scan frequency by the optical deflector; and a control unit that reads the defect inspection conditions stored for each inspection step in the storage unit and controls the driving of the stage unit and the optical deflector under the conditions.

6 Claims, 3 Drawing Sheets

SYSTEM AND METHOD OF TWO-STEPPED LASER SCATTERING DEFECT INSPECTION

Priority is claimed on Japanese Patent Application No. 2008-259804, filed Oct. 6, 2008, the content of which is incorporated herein by reference.

BACKGROUND OF THE INVENTION

1. Field of the Invention

The present invention relates to laser scattering defect inspection systems and methods for detecting small defects present on the surface of a workpiece using light scattering.

2. Description of the Related Art

In the related art, laser scattering defect inspection systems are known as systems for detecting small defects present on the surface of workpieces such as semiconductor wafers, patterned wafers, or mask blanks. The laser scattering defect inspection systems are configured to irradiate a laser beam on a wafer as the workpiece and detect light scattered from the surface, thereby detecting the presence of defects.

A spiral scanning defect inspection system, which is a typical defect inspection system, irradiates a laser beam on a wafer from a fixed position while rotating and transporting the wafer in a radial direction thereof, thereby scanning (spirally scanning) an entire surface of the wafer in a spiral form. Moreover, as effective methods of scanning a wafer surface, methods disclosed in U.S. Pat. Nos. 5,712,701, 6,118,525, 6,292,259, and PCT/US2005/045931 are known. This method employs a complex scanning method that scans (cross-scans) a beam irradiation position from the laser side, in addition to the spiral scan. Since this scanning method minutely vibrates the beam irradiation position using an optical deflector, the beam spot size can be increased substantially, and thus, the wafer surface can be scanned effectively with fewer revolutions per minute.

However, since the scanning methods disclosed in U.S. Pat. Nos. 5,712,701, 6,118,525, 6,292,259, and PCT/US2005/045931 are complicated, there is a problem that the positional precision of the detected defect coordinates is poor. For example, during the LSI process, it is common practice to examine the presence or the location of defects using an optical defect inspection system with high throughput and, based on the thus obtained information, to investigate and classify (actual condition investigation) the defects using a review SEM (scanning electron microscope). However, if the positional precision of the detected defect coordinates is poor, it may take a considerable amount of time to locate the defects, thus deteriorating the processing efficiency.

On the other hand, the defect inspection system is also used for the final shipment inspection which is performed at the stage of wafer shipment. The final shipment inspection is performed for all wafers, and the inspected wafers are generally packaged into a case for shipment without any further processing. In this case, the number of defects becomes important, and the positional precision of the defect coordinates is not taken into consideration. Since the final shipment inspection is a total inspection, it is important to reduce the inspection time per wafer.

SUMMARY OF THE INVENTION

The present invention has been made in view of the above-described circumstances and an object of the present invention is to provide a laser scattering defect inspection system and a laser scattering defect inspection method capable of effectively performing the defect inspection of workpieces.

In order to attain the object, according to a first aspect of the invention, there is disclosed a laser scattering defect inspection system that irradiates a laser beam on a surface of a workpiece to detect the light beam scattered from the surface, thereby detecting the presence of defects, the laser scattering defect inspection system including: a stage unit that rotates the workpiece and transports the workpiece in one direction; a laser light source that emits the laser beam toward the workpiece mounted on the stage unit; an optical deflector that scans the laser beam emitted from the laser light source on the workpiece; an optical detector that detects the laser beam scattered from the surface of the workpiece; a storage unit that stores defect inspection conditions for each inspection step of a manufacturing process of the workpiece, where the conditions include the rotation speed and the moving speed of the workpiece by the stage unit, the scan width on the workpiece and the scan frequency by the optical deflector; and a control unit that reads the defect inspection conditions stored for each inspection step in the storage unit and controls the driving of the stage unit and the optical deflector under the conditions.

Due to this configuration, the defect inspection of the workpiece can be performed under conditions appropriate for each inspection step. Therefore, it is possible to greatly reduce the time required for the defect inspection and improve the total efficiency of production processes including the inspection process.

In the laser scattering defect inspection system according to the above aspect of the invention, it is preferable that: the optical deflector is an acousto-optical deflector which includes an acousto-optical medium and a piezoelectric vibrator capable of causing an ultrasonic wave to propagate through the acousto-optical medium; and the control unit controls the scan width on the workpiece and the scan frequency by the optical deflector by controlling the vibration conditions of the piezoelectric vibrator.

Due to this configuration, since high-speed scanning of an order of MHz is made possible, the defects can be detected more efficiently compared to a method that mechanically controls the optical path of light as in the case of using galvano-mirrors, for example.

Moreover, according to a second aspect of the present invention, there is disclosed a laser scattering defect inspection method for detecting defects, including: a step of providing a complex scan combining a spiral scan that scans a laser beam on a workpiece in a spiral form by rotating and transporting the workpiece in one direction and a cross scan that deflects the laser beam using an optical deflector to be scanned on the workpiece; a step of scanning a surface of the workpiece to detect laser beams scattered from the surface of the workpiece; a first inspection step of performing defect inspection as a preliminary inspection for performing actual condition investigation; and a second inspection step of performing defect inspection that requires only the number of defects but does not require actual condition investigation, wherein: the scan width of the cross scan is controlled to be relatively small in the first inspection step; and, the scan width of the cross scan is controlled to be relatively large in the second inspection step.

According to this method, the defect inspection of the workpiece can be performed under appropriate conditions for each inspection step. Therefore, it is possible to reduce greatly the time required for the defect inspection and improve the total efficiency of production processes including the inspection process.

In the laser scattering defect inspection method according to the above aspect of the invention, it is preferable that the defect inspection in the first inspection step is performed under conditions such that the beam diameter on the workpiece is equal to or larger than 0.5 μm and equal to or smaller than 25 μm, and the scan width of the cross scan is zero. Moreover, it is preferable that the defect inspection in the second inspection step is performed under conditions such that the beam diameter on the workpiece is equal to or larger than 0.5 μm and equal to or smaller than 25 μm, the scan width of the cross scan is equal to or larger than the beam diameter and equal to or smaller than 5 mm, and the scan frequency of the cross scan is equal to or higher than 10 MHz and equal to or lower than 1,000 MHz.

According to this method, highly sensitive and highly efficient defect inspection can be achieved.

DETAILED DESCRIPTION OF THE INVENTION

Hereinafter, an embodiment of the present invention will be described with reference to the drawings. In the following description, the positional relationship of respective members will be described with the aid of an XYZ orthogonal coordinate system. A predetermined direction on a horizontal plane will be defined as the X direction, a direction orthogonal to the X direction on the horizontal direction will be defined as the Y direction, and a direction orthogonal, namely vertical, to both the X and Y directions will be defined as the Z direction.

Figure 1:
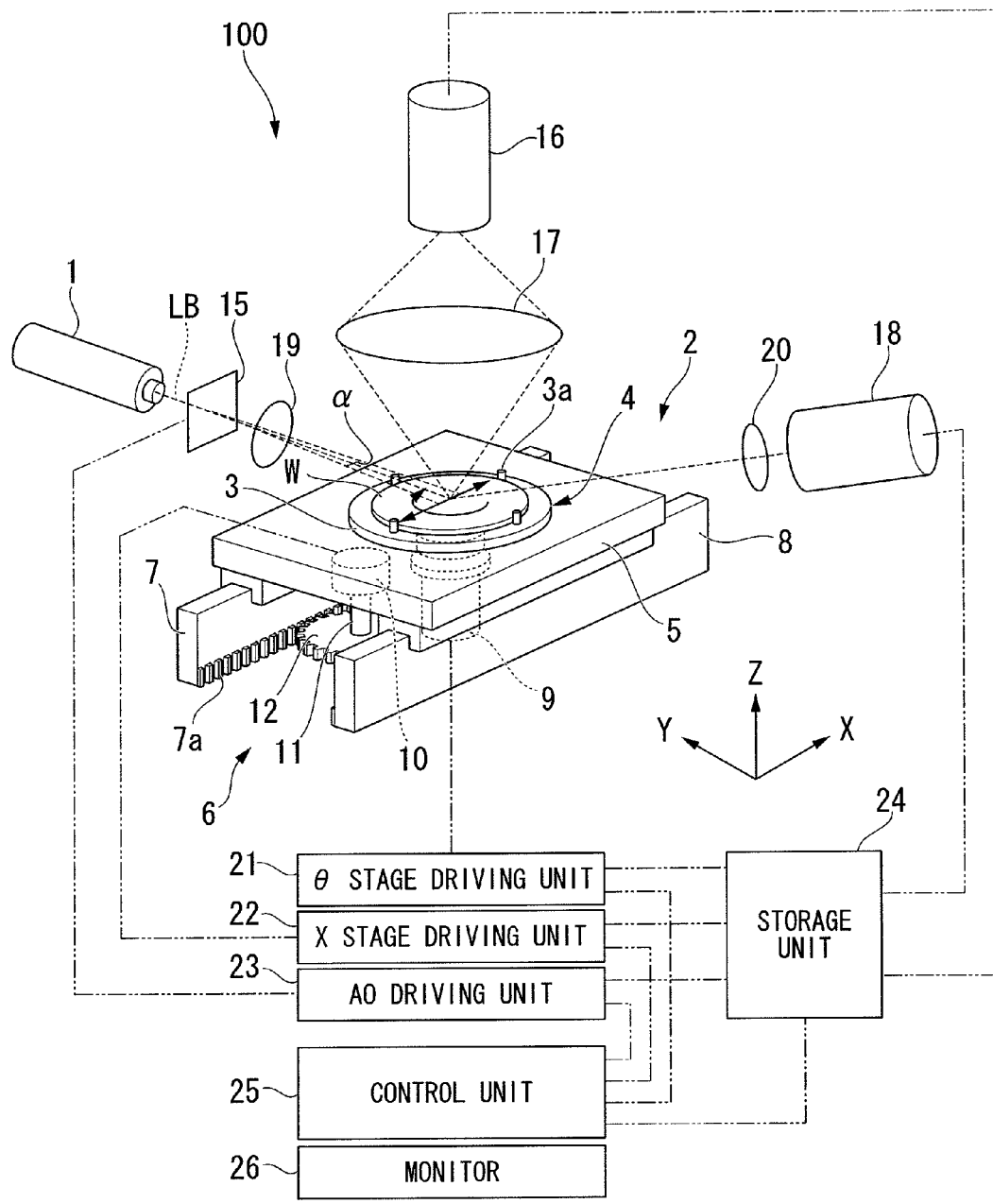
FIG. 1 is a schematic perspective view illustrating an example of a defect inspection system according to the present invention.

FIG. 1 is a schematic configuration view illustrating an example of a laser scattering defect inspection system 100 according to the present invention.

The defect inspection system 100 is for detection of small particles, defects, scratches, and the like present on the surface of workpieces such as semiconductor wafers, patterned wafers, or mask blanks. In the present embodiment, defect inspection is made of a semiconductor wafer W (blank wafer) of 300 mm diameter before performing an LSI manufacturing process.

The defect inspection system 100 includes a laser light source 1 such as a visible light laser or a ultra-violet light laser. The laser light source 1 irradiates a P-polarized laser beam LB toward the wafer W. The laser beam LB emitted from the laser light source 1 is deflected by an optical deflector 15, condensed by a lens 19 to around 10 μm, and then irradiated on the wafer W. The incidence angle of the laser beam LB is at 65 to 85 degrees, for example, from a normal direction (the Z-axis direction) of the wafer W, and the incidence direction of the laser beam LB is parallel to the Y direction.

The laser beam LB incident on the wafer W is partially scattered by light scattering objects, such as small particles, defects, or scratches, present on the surface of the wafer W. The scattered laser beam LB is focused by a lens 17 disposed above the wafer W to be detected by a first optical detector 16. The non-scattered laser beam LB (normally reflected laser beam LB) is focused by a lens 20 to be detected by a second optical detector 18 which is disposed in the direction of the normal reflection. As the optical detectors 16 and 18, photomultiplier tubes or photo-diodes may be used.

Although only one set of the lens 17 and the first optical detector 16 is illustrated in FIG. 1, it is preferable to provide a plurality of sets of the lens 17 and the first optical detector 16 so as to cover the upper side of the wafer W.

Moreover, although optical elements such as beam expanders or mirrors are additionally, and as necessary, disposed between the laser light source 1 and the optical deflector 15, the illustration thereof is omitted in FIG. 1.

The wafer W is mounted on a stage unit 2 which includes a rotating mechanism 4 and an X-directional transport mechanism 6. In the present embodiment, the stage unit 2 has formed thereon two guide rails 7 and 8 which extend in the X direction. An X stage 5 is mounted to slide on the guide rails 7 and 8. A motor 10 having a gear 12 and a shaft 11 for rotating the gear 12 is installed in the X stage 5. The gear 12 is engaged with a groove 7a that is formed on the inner surface of the guide rail 7, so that when the gear 12 is rotated by the motor 10, the X stage 5 is slid on the guide rails 7 and 8 in the X direction.

A θ stage 3 having a circular shape is mounted on the X stage 5. A motor 9 for rotating the θ stage 3 is installed in the θ stage 3. A plurality of flanges 3a for achieving the positioning of the wafer W is arranged at regular intervals so as to protrude outwardly from the outer circumference of the θ stage 3. The wafer W is fixed onto the θ stage 3 by a non-illustrated suction chuck in a state where the horizontal displacement thereof is restricted by the flanges 3a.

The rotation speed of the θ stage 3 and the X-directional moving speed of the X stage 5 are adjustably controlled by a θ stage driving unit 21 and an X stage driving unit 22, respectively. The rotation amount of the θ stage 3 and the X-directional movement amount of the X stage 5 are stored in a storage unit 24. The rotation amount of the θ stage 3 and the X-directional movement amount of the X stage 5 can be detected by an encoder which is connected to the motors 9 and 10, for example.

The optical deflector 15 for deflecting the laser beam LB in the X direction is disposed between the laser light source 1 and the stage unit 2. The beam spot on the wafer W is scanned in a direction parallel to the moving direction (the X direction) of the wafer W by the optical deflector 15.

The optical deflector 15 may employ various methods, such as a method that mechanically controls light or a method that controls the refractive index by using physical phenomena such as an acousto-optical effect, an electro-optical effect, or a thermo-optical effect. In the present embodiment, the optical deflector 15 employs an acousto-optical deflector capable of high-speed scanning of an order of MHz. The acousto-optical deflector is produced by attaching a piezoelectric vibrator to an acousto-optical medium made of glass or single crystals of tellurium dioxide ($TeO_2$), lead molybdate ($PbMoO_4$), or the like. The acousto-optical deflector is configured to apply an electrical signal to the piezoelectric vibrator to generate an ultrasonic wave to be propagated through the medium, thereby causing diffraction of a laser beam propagating through the medium.

The deflection angle α of the laser beam LB changes depending on the frequency of the ultrasonic wave. An AO driving unit 23 controls the frequency of the ultrasonic wave with the electrical signal supplied to the piezoelectric vibrator, thus controlling the shaped width (scan width) of the beam spot on the wafer W.

The beam spot position is calculated by an arithmetic unit such as a CPU provided to the control unit 25 based on the rotation amount of the θ stage 3, the movement amount of the X stage 5, the scan width of the beam spot by the optical deflector 15, and the like. The calculated beam spot position information is stored in the storage unit 24 together with the light intensity data detected by the first and second optical detectors 16 and 18. The control unit 25 detects the locations of the occurrence of light scattering on the wafer W, caused by light scattering objects such as particles, defects, or scratches, and detects the locations as light point defects (LPDs). Based on the detection results, the distribution of particles, defects, or scratches, present on the surface of the wafer W is detected.

Then, a user is able to observe in-plane distribution data of the LPDs on a monitor 26. Moreover, the in-plane distribution data of the LPDs may be used when investigating or classifying particles, defects, scratches, and the like on the wafer W with a scanning electron microscope which is also called a review SEM (scanning electron microscope).

Figure 2A:
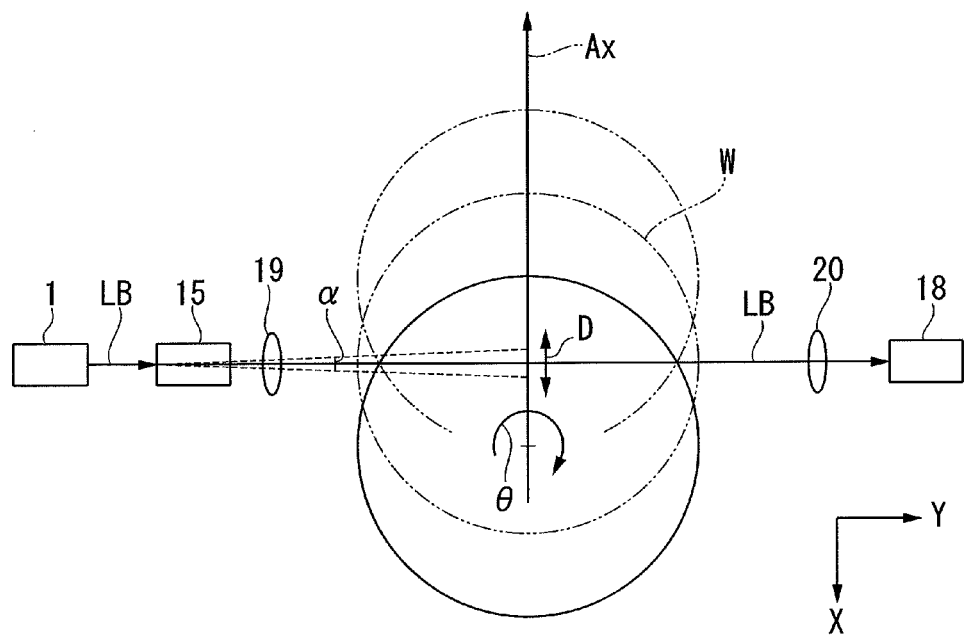
FIGS. 2A and 2B are schematic views for describing a method of scanning a laser beam on a wafer.
Figure 2B:
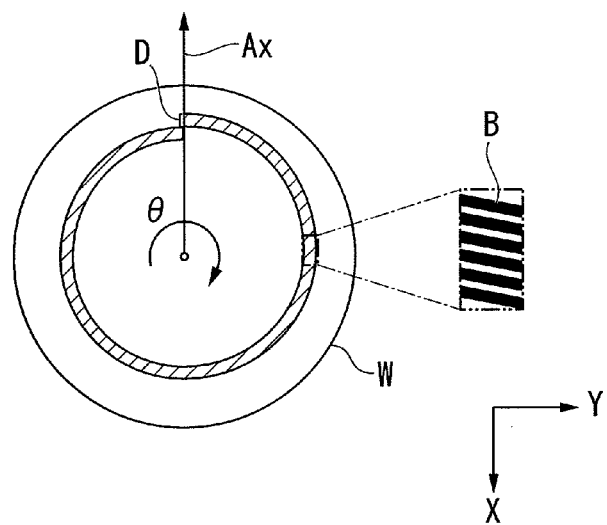

FIGS. 2A and 2B are schematic views for describing a method of scanning the laser beam LB on the wafer W. FIG. 2A is a plan view for describing the transportation state of the wafer W across the optical path of the laser beam LB, and FIG. 2B is a plan view illustrating the trajectory of the beam spot on the wafer surface.

As illustrated in FIG. 2A, in the defect inspection system 100 of the present embodiment, the optical system such as, for example, the laser light source 1, the optical deflector 15, and the like are arranged at a fixed position, the wafer W is moved relative to the optical system so that the laser beam is scanned over an entire inspection area of the wafer W. As a method of realizing the relative movement, a rotational movement of the wafer W and transportation of the wafer W in the radial direction (the X direction) on the rotation plane are used. That is to say, the wafer W is rotated and transported in the radial direction thereof, thus scanning (spirally scanning) the entire surface of the wafer W in a spiral form.

During the transportation of the wafer W, the laser beam LB emitted in the Y direction is deflected (cross-scanned) in the X direction by the optical detector 15. Therefore, as illustrated in FIG. 2B, the wafer W is spirally scanned with a beam having a scan width D which corresponds to the deflection angle α. The rotation speed and the X-directional moving speed of the wafer W are set so that the movement amount in the radial direction of the wafer W during one rotation of the wafer W is identical to the scan width D. In this way, it is possible to scan the entire inspection area of the wafer W without leaving any area unscanned.

The trajectory of the beam spot has a structure in which a plurality of strip-shaped lines B extending in the radial direction of the wafer W is arranged at regular intervals in the circumferential direction of the wafer W. Therefore, by performing such a spiral scan of the wafer W a plurality of times so as to bury the space between the strip-shaped lines B and B, the entire inspection area of the wafer can be scanned without leaving any area unscanned.

As described above, the position of the beam spot that scans on the wafer is calculated by the control unit 25 based on the rotation amount of the θ stage 3, the movement amount of the X stage 5, and the scan width of the cross scan. However, in a complex scanning method combining the spiral scan and the cross scan, since the scanning method is complicated, the positional precision of the detected defect coordinates (LPD coordinates) is poor, which may therefore cause a problem when performing actual condition investigation with a review SEM device. Although the positional precision of the defect coordinates can be improved by decreasing the scan width D of the cross scan, this method will increase the inspection time, which may therefore cause a problem when performing a total inspection of wafers during the final shipment inspection of wafers.

Therefore, in the defect inspection system 100 of the present embodiment, the scan width D of the cross scan is changed depending on the positional precision of defect coordinates which are required for each inspection step. For example, in the case (first inspection step) of performing a defect inspection as a preliminary inspection for performing actual condition investigation, the scan width D of the cross scan is decreased. On the other hand, in the case (second inspection step) of performing a defect inspection that only requires the number of defects but does not require the actual condition investigation, the scan width D of the cross scan is increased. By doing so, it is possible to reduce the time required for the defect inspection and improve the overall efficiency of production processes including an inspection process.

Figure 3A:
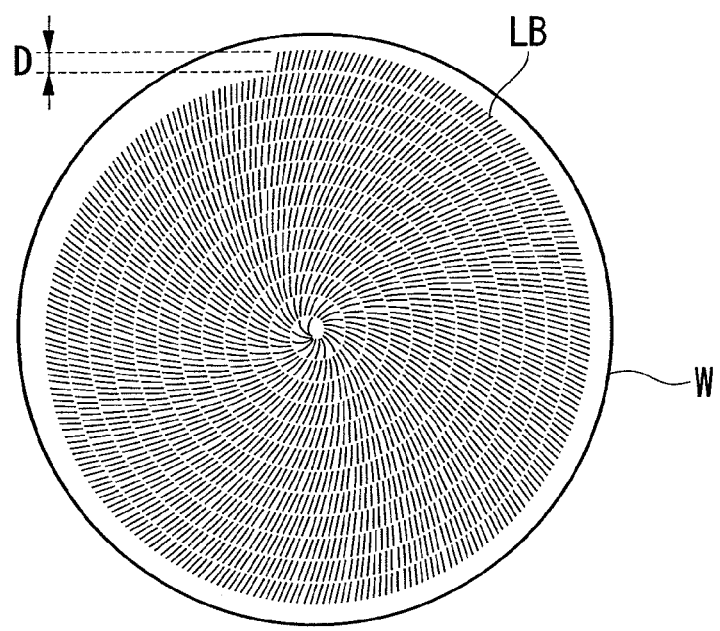
FIGS. 3A and 3B are top views illustrating examples of the conditions of defect inspection.
Figure 3B:
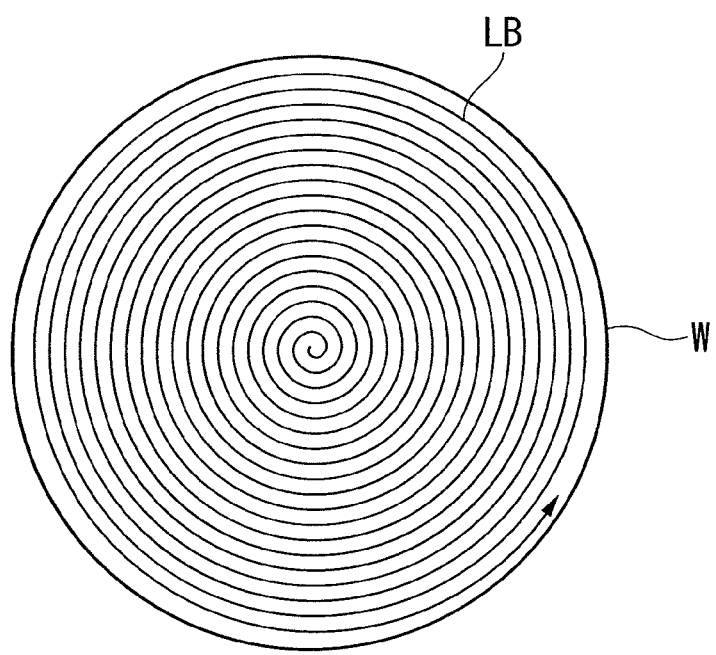

FIGS. 3A and 3B are plan views for describing the defect inspection performed in each inspection step. FIG. 3A is a view for describing the final shipment inspection which is performed at the shipment stage after the manufacture of wafers, and FIG. 3B is a view for describing the defect inspection which is performed as a preliminary inspection for performing a review SEM investigation during or prior to the manufacture of wafers.

As illustrated in FIG. 3A, in the final shipment inspection which is performed at the stage of wafer shipment, determination as to good or bad is made depending only on the number of defects. For this reason, it is only necessary to examine the number of defects and the positional precision of defect coordinates is not taken into consideration. Therefore, as a method of defect inspection, a complex scanning method combining the spiral scan and the cross scan is employed. For example, highly sensitive and highly efficient defect inspection can be achieved by controlling inspection conditions such that the beam diameter on the wafer W is controlled to be equal to or larger than 0.5 μm and equal to or smaller than 25 μm, the scan width D of the cross scan is controlled to be equal to or larger than the beam diameter and equal to or smaller than 5 mm, and the scan frequency of the cross scan is controlled to be equal to or higher than 10 MHz and equal to or lower than 1,000 MHz.

As illustrated in FIG. 3B, in the defect inspection which is performed as a preliminary inspection of the review SEM investigation, high positional precision of defect coordinates is required so that defect locations can be easily detected at the time of performing the actual condition investigation. For this reason, the cross scan of the optical deflector is stopped, or the scan width of the cross scan is restricted to a predetermined range so that defect locations can be easily detected at the time of performing the actual condition investigation. For example, highly sensitive and highly efficient defect inspection can be achieved by performing only the spiral scan under inspection conditions such that the beam diameter on the wafer W is controlled to be equal to or larger than 0.5 μm and equal to or smaller than 25 μm, and the scan width D of the cross scan is controlled to be zero.

The conditions for the defect inspection which is performed in each inspection step are stored for each inspection step in the storage unit 24. In the storage unit 24, the respective conditions, such as, for example, the beam diameter on the wafer W, the scan width of the cross scan, and the scan frequency of the cross scan, are stored for each inspection step, and the rotation speed of the θ stage and the moving speed of the X stage corresponding to these conditions are also stored for each inspection step.

The control unit 25 reads the inspection conditions of each inspection step from the storage unit 24 and displays them, for example, like "Inspection Mode 1" or "Inspection Mode 2"

on the monitor 26. Then, the user is able to set desired inspection conditions (the beam diameter on the wafer W, the scan width of the cross scan, the scan frequency of the cross scan, the rotation speed of the θ stage, and the moving speed of the X stage) by selecting a character or an icon of "Inspection Mode 1" or "Inspection Mode 2" displayed on the monitor 26.

The control unit 25 controls the θ stage driving unit 21, the X stage driving unit 22, and the AO driving unit 23 based on the inspection conditions selected by the user. The θ stage driving unit 21, the X stage driving unit 22, and the AO driving unit 23 drive the θ stage 3, the X stage 5, and the optical deflector 15, respectively, based on a control signal from the control unit 25, thereby performing the defect inspection under the selected inspection conditions.

According to the defect inspection system 100 having such a configuration, the defect inspection of the wafer W can be performed under appropriate conditions for each inspection step. Therefore, it is possible to reduce greatly the time required for defect inspection and improve the total efficiency of production processes including the inspection process.

EXAMPLE

As the final shipment inspection of wafers, a complex scanning method of a spiral scan and a cross scan was conducted. A spiral scan with a spot size of 10 μm was performed under conditions where the rotation speed of the θ stage was set to 2,000 rpm (revolutions per minute), the scan frequency of the cross scan was set to 40 MHz (the maximum rotational movement distance per scan was 0.785 μm), and the scan width of the cross scan was set to 150 μm. In this case, the processing capability was 60 wph (wafers per hour) (without including wafer transportation time and signal processing time). Using an ultraviolet light laser having a wavelength of 355 nm, a P-polarized laser beam was made incident at an angle of 70 degrees as measured from the normal direction of the wafer to the Y direction. In this method, the minimum detection size of PSL (polystyrene-latex) was 28 nm. Moreover, the positional precision of the LPD coordinates relative to the review SEM device was less than 100 μm.

As the preliminary inspection of the review SEM investigation, only the spiral scan was conducted. A spiral scan with a spot size of 10 μm was performed twice in an overlapping manner on the entire area of the wafer under conditions where the rotation speed of the θ stage was set to 3,000 rpm, and the scan width of the cross scan was set to zero. In this case, the processing capability was 6 wph (without including wafer transportation time and signal processing time). Using an ultraviolet light laser having a wavelength of 355 nm, a P-polarized laser beam was made incident at an angle of 70 degrees as measured from the normal direction of the wafer to the Y direction. In this method, the minimum detection size of PSL was 28 nm. Moreover, the positional precision of the LPD coordinates relative to the review SEM device was less than 20 μm.

COMPARATIVE EXAMPLE 1

The defect inspection was conducted using a commercially available defect inspection system A. The defect inspection system A is a spiral scanning defect inspection system which does not have an optical deflector. A spiral scan with a spot size of 50 μm was performed twice in an overlapping manner on the entire area of the wafer under conditions where the rotation speed was set to 2,000 rpm. In this case, the processing capability was 20 wph (without including wafer transportation time and signal processing time). Using an ultraviolet light laser having a wavelength of 355 nm, a P-polarized laser beam was made incident at an angle of 70 degrees as measured from the normal direction of the wafer to the Y direction. In this method, the minimum detection size of PSL was 37 nm. Moreover, the positional precision of the LPD coordinates relative to the review SEM device was less than 40 μm.

In Comparative Example 1, since the final shipment inspection of wafers and the preliminary inspection of the review SEM investigation are performed under the same conditions, the former inspection cannot achieve sufficiently high processing efficiency, and the latter inspection takes a considerable amount of time for detecting defect locations. Therefore, the total processing efficiency will be lower than that of Example.

COMPARATIVE EXAMPLE 2

The defect inspection was conducted using a commercially available defect inspection system B. The defect inspection system B is a defect inspection system for inspection of small-diameter wafers of up to 200 mm and is configured to scan the entire area of a wafer by the combination of a laser-side X scan where a single-axis galvano-mirror having a low scan speed is used as a deflection element and a stage-side Y scan. Since this system has a structure that scans the entire surface along the X direction, due to the difference in the incidence angle on the wafer and the laser beam path, drawbacks were observed that the sensitivity on the wafer plane is likely to change in the X direction. Therefore, this system may find difficulties in application to large-diameter wafers of up to 300 mm. Using a visible light laser having a wavelength of 488 nm, a P-polarized laser beam was made incident at an angle of 70 degrees as measured from the normal direction of the wafer to the Y direction. In this method, the minimum detection size of PSL was 100 nm. Moreover, the positional precision of the LPD coordinates relative to the review SEM device was poor and was at least equal to or larger than 400 μm.

COMPARATIVE EXAMPLE 3

The defect inspection was conducted using a commercially available defect inspection system C. The defect inspection system C employs a complex scanning method combining a spiral scan and a cross scan. A spiral scan with a spot size of 30 μm was performed twice in an overlapping manner on the entire area of the wafer under conditions where the lowest rotation speed (at the circumferential portion) was set to 50 rpm, the highest rotation speed (at the center) was set to 200 rpm (the average rotation speed was 125 rpm, the scan frequency of the galvano-mirror, which is the optical deflector, was set to 1.5 kHz (the rotational movement distance per scan was 50 μm), and the beam scan width on the wafer was set to 4 mm so that the scan widths overlapped one another. In this case, the processing capability was 100 wph (without including wafer transportation time and signal processing time). Using a visible light laser having a wavelength of 532 nm, a P-polarized laser beam was made incident at an angle of 65 degrees as measured from the normal direction of the wafer to the Y direction. In this method, the minimum detection size of PSL was 45 nm. Moreover, the positional precision of the LPD coordinates relative to the review SEM device was poor and was at least equal to or larger than 600 μm.

In Comparative Example 3, since the final shipment inspection of wafers and the preliminary inspection of the review SEM investigation are performed under the same conditions, the latter inspection takes a considerable amount of time for detecting defect locations. Therefore, the total processing efficiency will be lower than that of Example.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A laser scattering defect inspection system that irradiates a laser beam on a surface of a workpiece to detect the light beam scattered from the surface, thereby detecting presence of defects, the laser scattering defect inspection system comprising:
    a stage mover that rotates the workpiece and transports the workpiece in one direction;
    a laser light source that emits the laser beam that has a beam diameter toward the workpiece mounted on the stage mover;
    an optical deflector that cross scans the laser beam emitted from the laser light source on the workpiece, where a scan width of a cross scan is a quantity of laser beam movement caused by the optical deflector;
    an optical detector that detects the laser beam scattered from the surface of the workpiece;
    a storage that stores defect inspection conditions for each of a plurality of inspections of the workpiece in a manufacturing process, where the conditions include a rotation speed and a moving speed of the workpiece by the stage mover, a scan width on the workpiece and a scan frequency by the optical deflector; and
    a controller that reads the defect inspection conditions stored for each of a plurality of inspections of the workpiece in the storage and controls the driving of the stage mover and the optical deflector under the conditions,
    wherein the controller controls the stage mover, the laser light source, the optical deflector and the optical detector, and
    the controller performs a first inspection step of defect inspection as a preliminary inspection for performing actual condition investigation, which classifies the defects, and a second inspection step of defect inspection that only counts a quantity of the defects but does not perform actual condition investigation, which classifies the defects,
    the optical deflector stops the cross scan when the controller performs the first inspection step, while the stage mover rotates and transports the workpiece and the optical detector detects the laser beam scattered from the surface of the workpiece, and
    the scan width of the cross scan is controlled to be equal or larger than the beam diameter on the workpiece in the second inspection step, while the stage mover rotates and transports the workpiece and the optical detector detects the laser beam scattered from the surface of the workpiece.

2. The laser scattering defect inspection system according to claim 1, wherein:
    the optical deflector is an acousto-optical deflector which comprises an acousto-optical medium and a piezoelectric vibrator capable of causing an ultrasonic wave to propagate through the acousto-optical medium; and,
    the controller controls the scan width on the workpiece and the scan frequency by the optical deflector by controlling the vibration conditions of the piezo-electric vibrator.

3. A laser scattering defect inspection method for detecting defects, comprising:
    providing a complex scan combining a spiral scan that scans a laser beam with a beam diameter on a workpiece in a spiral form by rotating and transporting the workpiece in one direction and a cross scan that deflects the laser beam using an optical deflector to be scanned on the workpiece, where a scan width of the cross scan is a quantity of laser beam movement caused by the optical deflector;
    scanning a surface of the workpiece to detect laser beams scattered from the surface of the workpiece;
    a first inspection step of performing defect inspection as a preliminary inspection for performing actual condition investigation, which classifies the defects; and
    a second inspection step of performing defect inspection that only counts a quantity of the defects but does not perform actual condition investigation, which classifies the defects, wherein:
    the cross scan of the optical deflector is stopped in the first inspection step, while the workpiece is rotated and transported and the laser beam scattered from the surface of the workpiece is detected; and
    the scan width of the cross scan is controlled to be equal or larger than the beam diameter on the workpiece in the second inspection step, while the workpiece is rotated and transported and the laser beam scattered from the surface of the workpiece is detected.

4. The laser scattering defect inspection method according to claim 3, wherein the first inspection step is performed while the beam diameter on the workpiece is equal to or larger than 0.5 µm and equal to or smaller than 25 µm.

5. The laser scattering defect inspection method according to claim 3, wherein the second inspection step is performed while the beam diameter on the workpiece is equal to or larger than 0.5 µm and equal to or smaller than 25 µm, the scan width of the cross scan is equal to or larger than the beam diameter and equal to or smaller than 5 mm, and a scan frequency of the cross scan is equal to or higher than 10 MHz and equal to or lower than 1,000 MHz.

6. The laser scattering defect inspection method according to claim 4, wherein the second inspection step is performed while the beam diameter on the workpiece is equal to or larger than 0.5 µm and equal to or smaller than 25 µm, the scan width of the cross scan is equal to or larger than the beam diameter and equal to or smaller than 5 mm, and the scan frequency of the cross scan is equal to or higher than 10 MHz and equal to or lower than 1,000 MHz.

* * * * *